(12) United States Patent
Hoffman

(10) Patent No.: US 9,056,005 B2
(45) Date of Patent: Jun. 16, 2015

(54) METHODS AND DEVICES FOR ARYTENOID REPOSITIONING

(75) Inventor: Henry T. Hoffman, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 13/201,669

(22) PCT Filed: Mar. 19, 2010

(86) PCT No.: PCT/US2010/027995
§ 371 (c)(1),
(2), (4) Date: Aug. 16, 2011

(87) PCT Pub. No.: WO2010/111140
PCT Pub. Date: Sep. 30, 2010

(65) Prior Publication Data
US 2011/0301580 A1 Dec. 8, 2011

Related U.S. Application Data

(60) Provisional application No. 61/163,300, filed on Mar. 25, 2009.

(51) Int. Cl.
*A61F 2/20* (2006.01)
(52) U.S. Cl.
CPC ....................... *A61F 2/20* (2013.01)

(58) Field of Classification Search
CPC ........................................................ A61F 2/20
USPC .............................................................. 623/9
See application file for complete search history.

(56) References Cited

U.S. PATENT DOCUMENTS

| | | | |
|---|---|---|---|
| 5,197,482 A * | 3/1993 | Rank et al. | 600/562 |
| 5,306,298 A * | 4/1994 | Godley et al. | 623/9 |
| 5,326,375 A | 7/1994 | Montgomery et al. | |
| 5,437,266 A * | 8/1995 | McPherson et al. | 600/217 |
| 5,531,752 A * | 7/1996 | Netterville et al. | 606/99 |
| 5,549,673 A * | 8/1996 | Beale | 623/9 |
| 5,593,439 A * | 1/1997 | Cummings et al. | 623/9 |
| 5,693,096 A * | 12/1997 | Bettez et al. | 623/9 |
| 5,855,607 A * | 1/1999 | Friedrich | 623/9 |
| 6,986,784 B1 | 1/2006 | Weiser et al. | |
| 2004/0254520 A1 | 12/2004 | Porteous et al. | |
| 2004/0254642 A1* | 12/2004 | Isshiki et al. | 623/11.11 |
| 2006/0200190 A1 | 9/2006 | Lorenzo et al. | |
| 2008/0023012 A1 | 1/2008 | Dineen et al. | |
| 2008/0071230 A1 | 3/2008 | Lindenthaler | |
| 2008/0140203 A1 | 6/2008 | Davis | |
| 2008/0188931 A1 | 8/2008 | Kwon | |
| 2009/0044814 A1 | 2/2009 | Iancea et al. | |
| 2010/0023125 A1* | 1/2010 | Debry et al. | 623/14.11 |
| 2012/0150293 A1* | 6/2012 | Hoffman et al. | 623/9 |

OTHER PUBLICATIONS

International Search Report and Written Opinion for PCT/US2010/027995 dated Oct. 27, 2010.

* cited by examiner

*Primary Examiner* — David Bates
(74) *Attorney, Agent, or Firm* — Peter K. Sollins; Foley Hoag LLP

(57) ABSTRACT

Methods and devices for repositioning the arytenoid cartilage of a human subject are disclosed.

15 Claims, 10 Drawing Sheets

Anterior View

Figure 1 -- Prior art

Superior View

Anterior View

METHODS AND DEVICES FOR ARYTENOID REPOSITIONING

CROSS-REFERENCE TO RELATED APPLICATIONS

This is the national stage of International application Ser. No. PCT/US2010/027995, filed Mar. 19, 2010, which claims the benefit of U.S. provisional application Ser. No. 61/163, 300, filed Mar. 25, 2009, which is hereby incorporated herein by reference.

SUMMARY

Methods and devices for repositioning the arytenoid cartilage of a human subject are disclosed.

DETAILED DESCRIPTION

Figure 1:
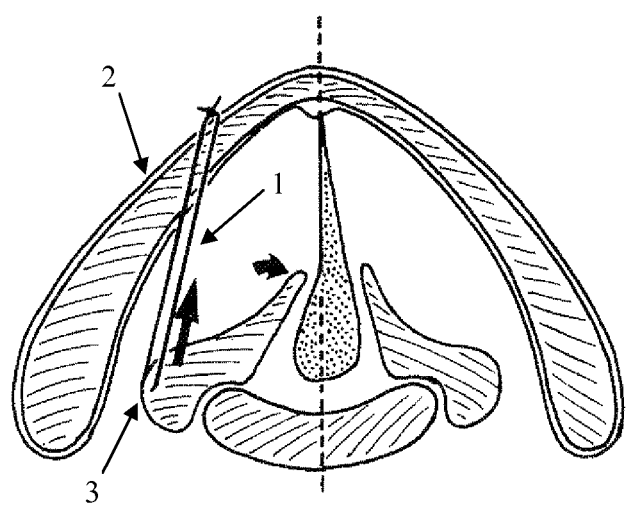
FIG. 1 shows a prior art method of vocal cord adduction.

FIG. 1 illustrates a method of arytenoid adduction in the prior art, as well as a superior view of the area of the thyroid and arytenoid cartilage in a human. According to this prior art, a suture 1 is placed through holes in both the thyroid cartilage 2 and the arytenoid muscular process 3. The ARD and related methods disclosed here improves on this and other prior art in several ways. First, the suture-based prior art shown in FIG. 1 can pull the arytenoid muscular process toward the thyroid cartilage but cannot push the arytenoid muscular process away from the thyroid cartilage; the ARD can do both. Similarly the prior art shown in FIG. 1 can only exert a force on the arytenoid along the direction of the suture while the ARD can reposition the arytenoid in any of several dimensions by rotation, and/or translation. Second, the ARD can be utilized in a far less invasive surgery than the prior art. Some prior art arytenoid adduction procedures involve remove large sections of the thyroid cartilage, e.g. U.S. Pat. No. 5,593,439 to Cummings, et al. (hereafter "Cummings"). By contrast, using the ARD typically requires making only a small (roughly 2 centimeter) incision in the skin and a small (a few millimeters) hole in the cricothyroid membrane. Third, in the prior art methods, once the holes for the suture have been formed, those holes cannot be moved. The ARD can engage the arytenoid or its muscular insertions and, if the position is not optimal, disengage and reengage to correct the position of engagement. Fourth, after the ARD is used, relatively little foreign matter is left implanted in the patient. In some embodiments, only the ARD and a fastener are left implanted in the patient. By contrast in Cummings, for example, an anchor flange is press-fitted into a hole drilled in the thyroid cartilage and left in the patient.

Figure 2:
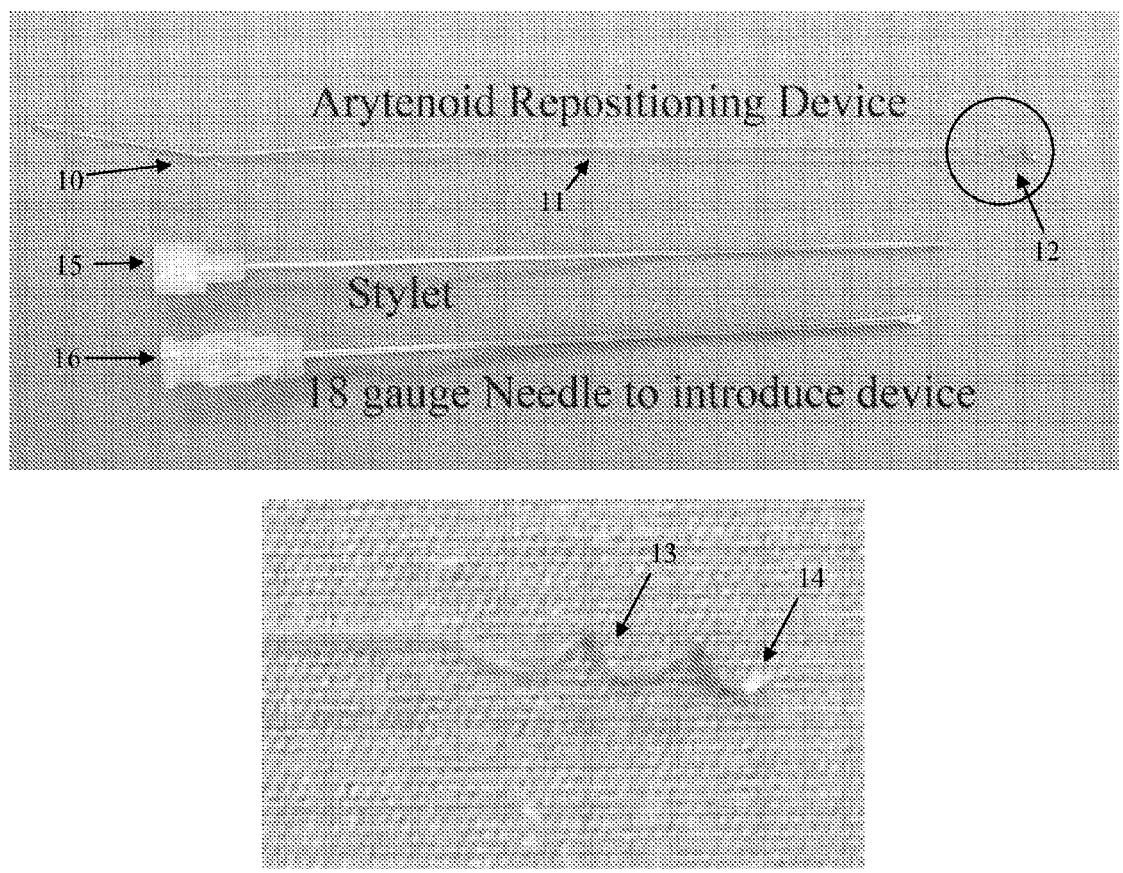
FIG. 2 shows one embodiment of the arytenoid repositioning device (ARD) and a close-up of the circled detail.

FIG. 2 shows one embodiment of an ARD as part of a kit of tools. The ARD 10 is shown at the top of FIG. 2. The ARD 10 as shown is made of a monolithic biocompatible titanium wire. The proximal portion 11 is shown on the left, uncoiled with a small recess near the end. The wire may define multiple recesses positioned along its proximal portion 11. Also, instead of or in addition to a recess, the proximal portion 11 of the wire may include one or more protrusions positioned along its proximal portion. The proximal portion 11 is shown extending substantially straight, defining an axis. The proximal portion is pliable so that a user may bend it. The proximal portion 11 should have pliability similar to a paper clip so that a one can easily bend the proximal portion 11 with one's fingers. Once bent so that a part of the proximal portion 11 is not co-linear with the original axis, the bent portion can be used as a lever to facilitate rotation of the ARD. The bent "handle" acts as a torque lever to provide mechanical advantage when the user twists the ARD. The proximal portion 11 is also capable of being trimmed by a surgeon during use.

The distal portion 12, as shown on the right of FIG. 2, may include a coil 13. The sharp distal tip 14 is shown at the far right of the ARD 10. The tip 14 is sharp enough to pierce cartilage, but can also be used to pierce muscle and/or tendinous tissue. The ARD embodiment shown is about 3 inches long from proximal to distal end. When applied to a typical human subject, 3 inches is long enough to allow the distal end to engage the arytenoid while leaving the proximal end exterior to the paraglottic space, even when the ARD 10 is advanced as much as 10 millimeters. The 3-inch length is also sufficient to allow the distal end of the ARD 10 to engage the arytenoid while the proximal end remains outside the paraglottic space. Since human subjects' paraglottic spaces vary in size, ARDs of different lengths may be better suited to some human subjects than to others. The ARD should be long enough to further allow the user to make a bend in the proximal portion as described above, to give the user leverage in rotating the ARD with the bent handle portion remaining outside the paraglottic space.

The kit as shown in FIG. 2 includes a trocar in the form of an 18 gauge needle 15. The trocar 15 is open at its proximal and distal ends, and defines an interior lumen. The ARD 10 and trocar 15 are shown to be sized so that the entire ARD 10 can pass through the interior of the trocar 15. The kit also includes a stylet 16 sized for insertion into the trocar 15. The kit could also include one or more fasteners. The fasteners could be adapted for securing the ARD 10 to a cartilage of the subject.

Figure 3:
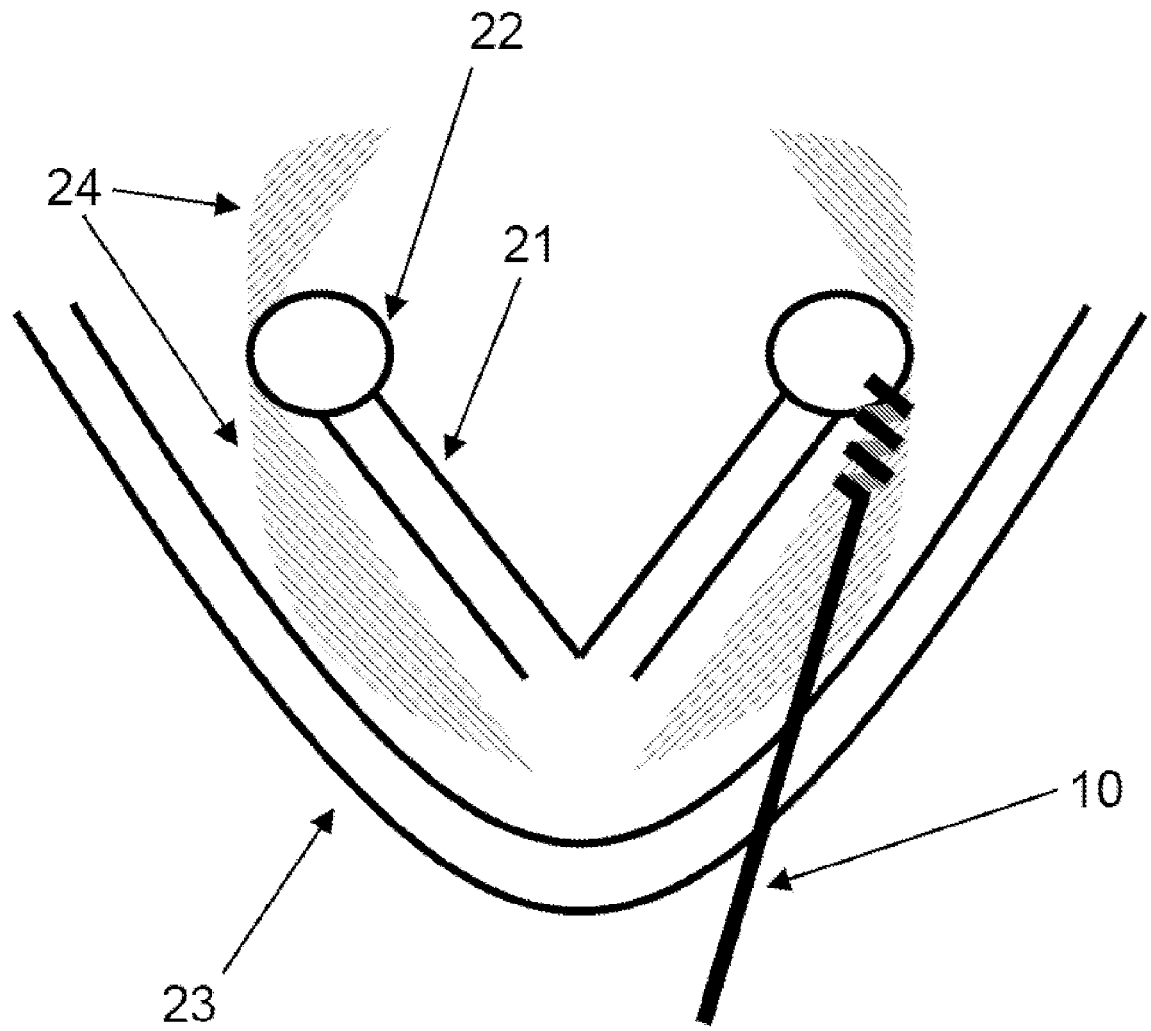
FIGS. 3 & 4 show schematic drawings of a human larynx with an ARD laid over the drawing to show how the ARD might be positioned and fastened in a human subject.

FIG. 3 shows an ARD 10 overlaid on a superior view of a human larynx and vocal cords 21. The V-shaped structure represents the vocal cords 21; the circles represent the arytenoids 22; the U-shaped structure represents the cricoid cartilage 23. The ARD 10 shown is sized so that the proximal end is capable of extending beyond the cricothyroid membrane while the distal end engages the arytenoid 22. Extending away from the arytenoids are the cricoarytenoid muscles 24. The ARD 10 is shown passing through the cricoid cartilage 23 substantially non-perpendicular to the cricoid or thyroid cartilage.

Figure 4:
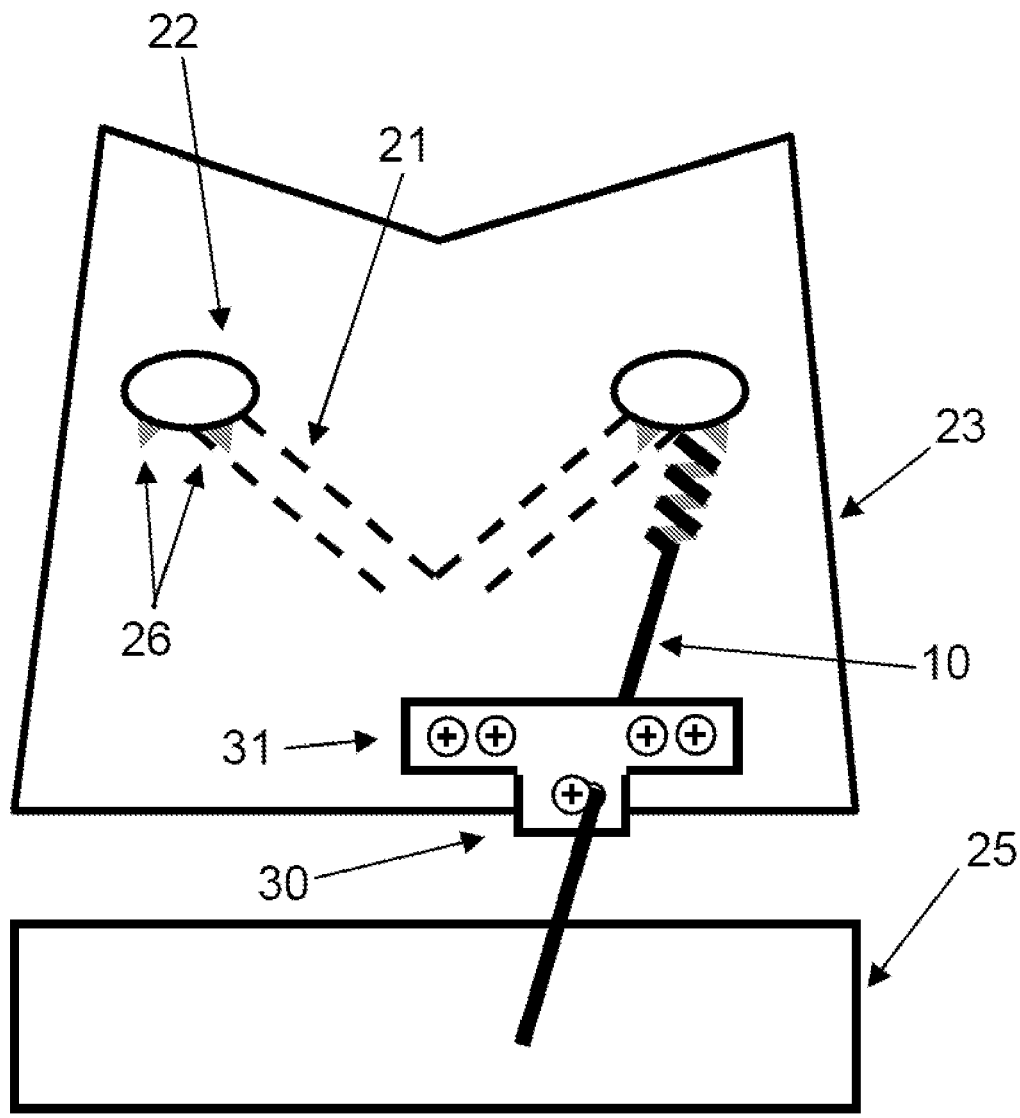

FIG. 4 shows an ARD 10 overlaid on an anterior view of a human larynx. At the bottom of FIG. 4 is the cricoid cartilage 25. Above the cricoid cartilage 25 is a space filled by the cricothyroid membrane. Above the membrane is the thyroid cartilage 23. Behind the thyroid cartilage 23 in dotted lines are shown the vocal ligaments 21. Above the vocal ligaments 21 are shown the right and left arytenoid 22, each with muscular insertions from the thyroarytenoid and cricoarytenoid muscles 26. The ARD 10 is shown as if it were engaging the muscular process or one of the muscular insertions 26. The ARD 10 has been positioned as if it were passing through the cricothyroid membrane, above the cricoid cartilage 25 and below the thyroid cartilage 23, into the paraglottic space. The ARD 10 has been secured by clamping the proximal portion between the thyroid cartilage and a plate 30 held to the cartilage with screws 31.

Fasteners secured to the proximal end of the ARD can take a variety of forms. The fasteners could be any device capable of being secured to both the ARD and a tissue of the patient. The fastener could be held snugly against the cricothyroid membrane by tension. The fastener could be secured to a cartilage, for example, the thyroid cartilage. The fastener could also be secured to a cartilage by a variety of couplers such as screws, sutures, plates, clips or adhesives.

Figure 5:
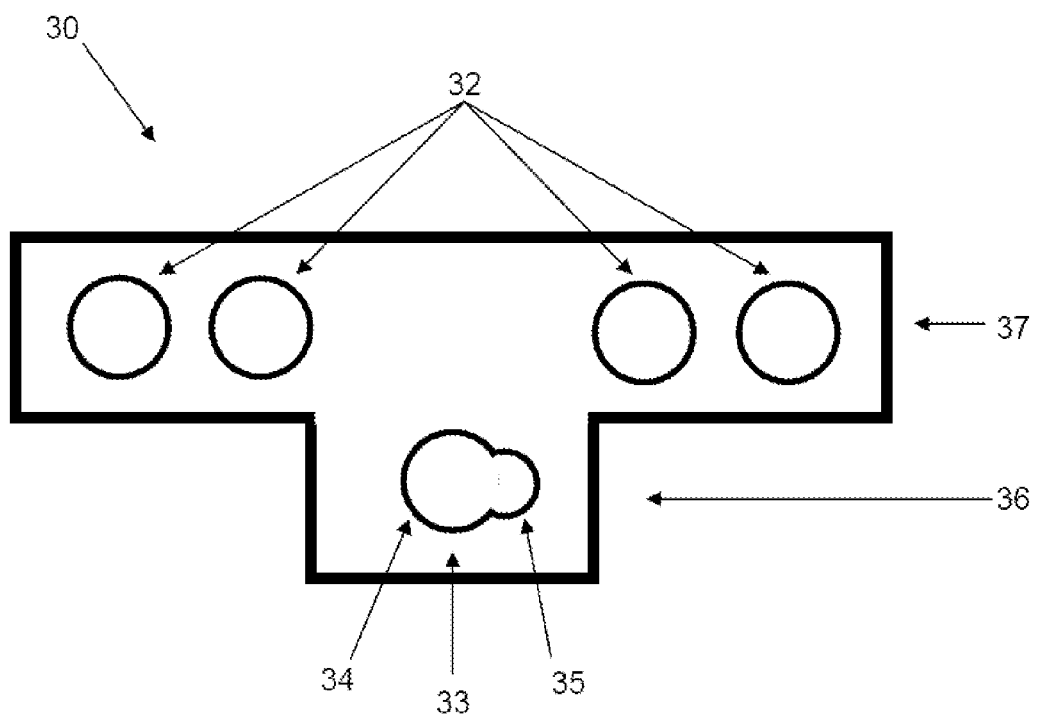
FIG. 5 shows an example of a fastener to be used with the ARD.

FIG. 5 shows a plate 30 that may be used as a fastener to secure the ARD. A plate may define one or more throughholes sized and shaped to pass and secure couplers (e.g., to pass screw shafts but not screw heads). The illustrated plate includes four such through holes 32. The illustrated plate also has a fifth hole 33 that is large enough to pass and secure both a coupler and the proximal portion of the ARD. A variety of shapes are possible; FIG. 5 shows a hole 33 having both an ordinary opening for a screw 34, and a secondary contiguous opening 35 designed to fit the proximal portion of the ARD. The fifth hole 33 is located on a tab 36 extending below the upper rectangular portion of the plate 37. To secure the ARD, the proximal portion of the ARD passes through the secondary opening 35, underneath the upper portion of the plate 37. Then screws are driven into the thyroid cartilage through the four ordinary screw holes 32 and through the screw-hole portion 34 of the fifth hole 33, and tightened so as to clamp the proximal portion of the ARD between the plate and the cartilage. Alternatively, the plate 30 may be secured with sutures instead of screws. Sutures may be preferred if the cartilage is un-ossified, as in children. The plate may be made of metal, plastic, or any other suitable biocompatible material.

Figure 6:
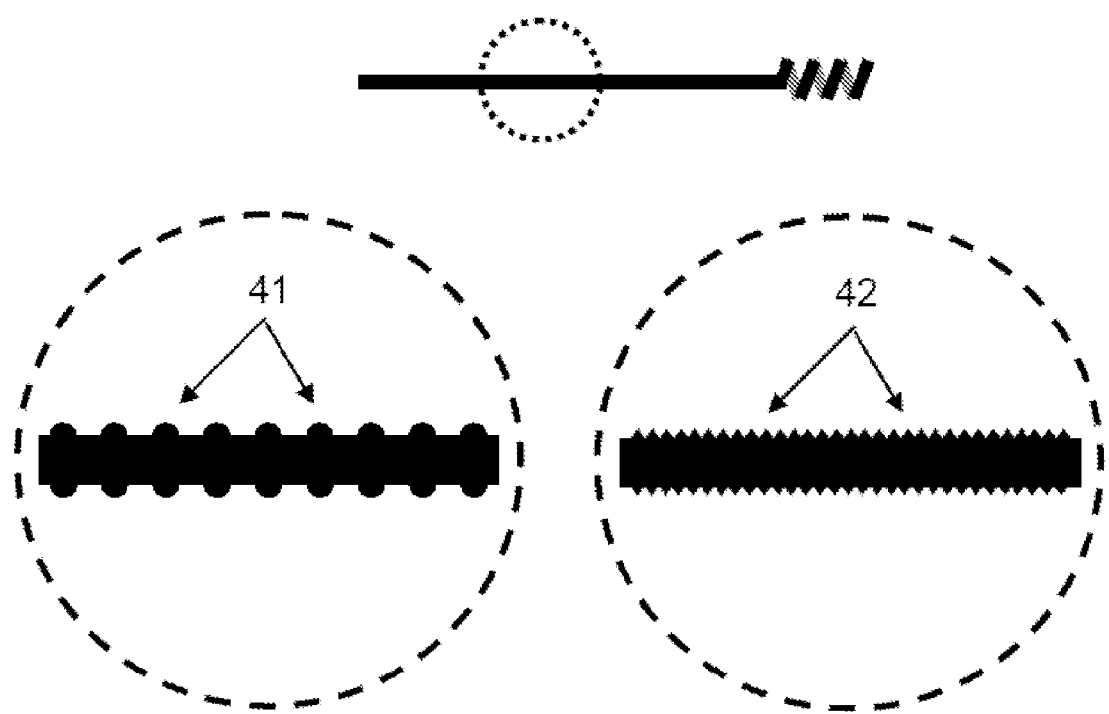
FIG. 6 shows two examples of the shaft of the ARD.

FIG. 6 shows the ARD with close-ups of two possible modifications of the ARD's proximal portion to improve its clamping in the plate. The close-up on the left shows rounded bumps 41 protruding from the proximal portion; the close-up on the right shows alternating ridges and valleys 42. Protrusions and indentations of any kind will help keep the ARD secured in the secondary opening 35. Alternatively, the ARD may be made of material that is sufficiently malleable as to be deformed when clamped between the plate and the thyroid. A bend or crimp in the ARD caused by tightening down the plate will also help keep the ARD secured in the secondary opening.

Figure 7:
FIGS. 7 & 8 show CT scans of a cadaveric human larynx with an ARD implanted.

FIG. 7 shows a CT scan of an actual human cadaveric larynx with an ARD with its distal end engaged with the arytenoid and its proximal end secured to the thyroid cartilage. The view is from the left side of the larynx and the ARD is engaged with the left arytenoid. In this case, hemoclips were affixed to the proximal end, and the hemoclips were used to secure the ARD to the thyroid cartilage. In an actual clinical use of the ARD, the proximal end of the ARD could be trimmed so that it would not extend substantially proximally beyond whatever fixation mechanism was used to secure the ARD in the subject. In an actual clinical use, any of a variety of methods could be used to both affix a fastener to the ARD and secure the ARD to a relatively immobile portion of the patient's larynx, for example, the thyroid cartilage.

As noted above, the ARD has the benefit over the prior art that relatively little foreign matter is left implanted in the patient after surgery. Only the ARD and the fasteners are left permanently implanted in the patient. In some embodiments, the ARD consists of the wire and the fastener or fasteners. In other embodiments, the ARD consists essentially of the wire and the fastener or fasteners.

Figure 8:
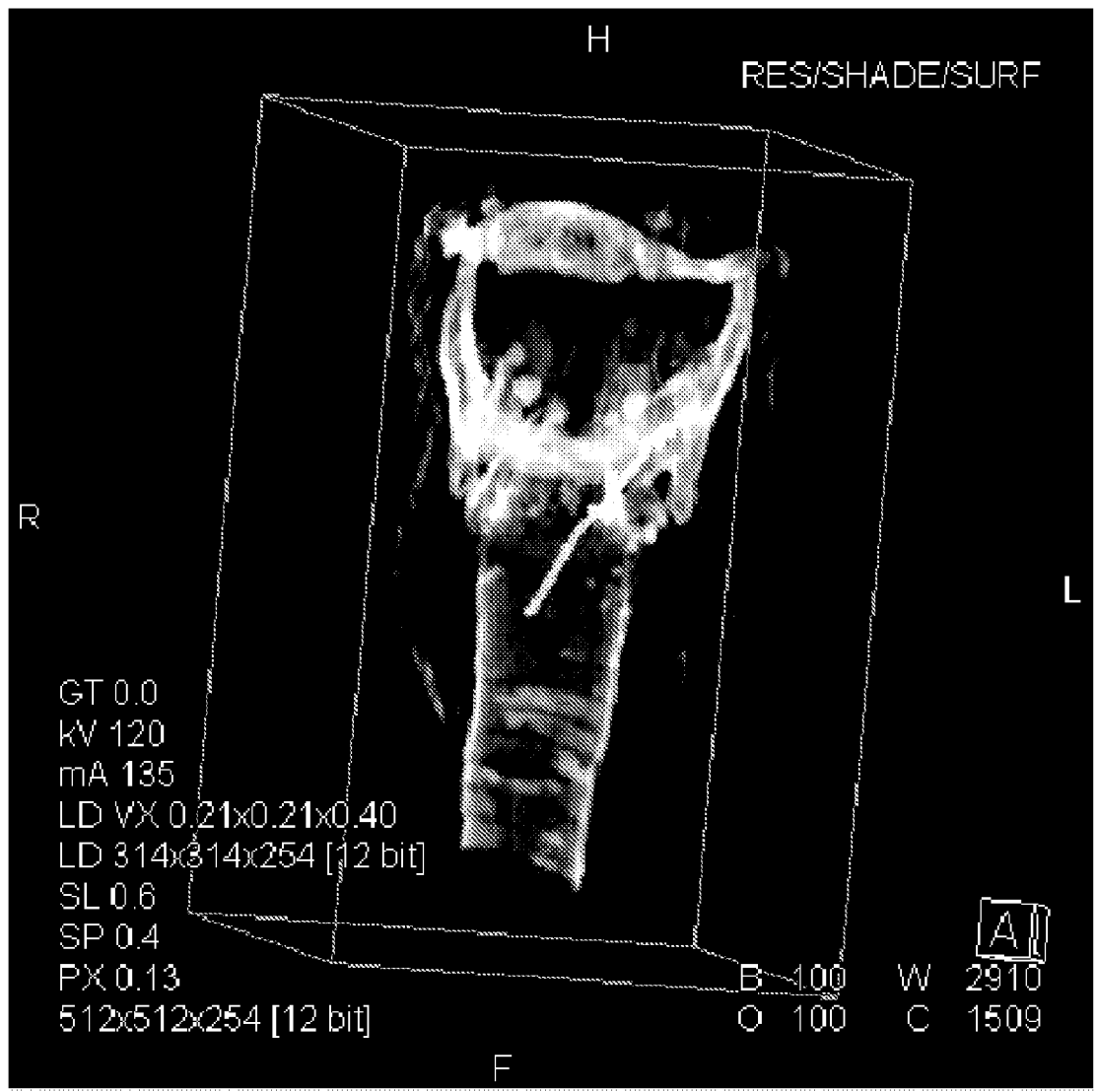

FIG. 8 shows an anterior view of the implanted ARD in the cadaveric larynx. The anterior view shows that the ARD is inserted through the cricothyroid membrane, above the cricoid cartilage and below the thyroid cartilage.

FIGS. 3-8 show how the ARD can be used to reposition the arytenoid of a subject. An incision in the neck could be made to access the subject's cricothyroid membrane, and the ARD advanced through the incision. Then the ARD could be advanced through the cricothyroid membrane. This could be done by piercing the membrane with a trocar and advancing the ARD through the trocar. Or the ARD could be advanced through the cricothyroid membrane without a trocar. Once through the cricothyroid membrane, the ARD will have entered the paraglottic space. The ARD could then be advanced through the paraglottic space to the neighborhood of the arytenoid. The ARD could then engage the arytenoid muscular process, or the thyroarytenoid or cricoarytenoid muscular insertions. Once engaged, the ARD can be moved in order to reposition, either by translation or rotation, the arytenoid. After the arytenoid has been beneficially repositioned, the ARD may be secured by affixing one or more fasteners to the one or more recesses or protrusions in the proximal portion of the ARD. The fastener or fasteners could be positioned anterior to the cricothyroid membrane and could fit snugly against an anterior aspect of the cricothyroid membrane. The fastener or fasteners could secure the ARD to a cartilage, possibly the thyroid cartilage. Using this method it would be possible to reposition the arytenoid leaving only the ARD and fastener or fasteners permanently implanted in the subject.

Figure 9:
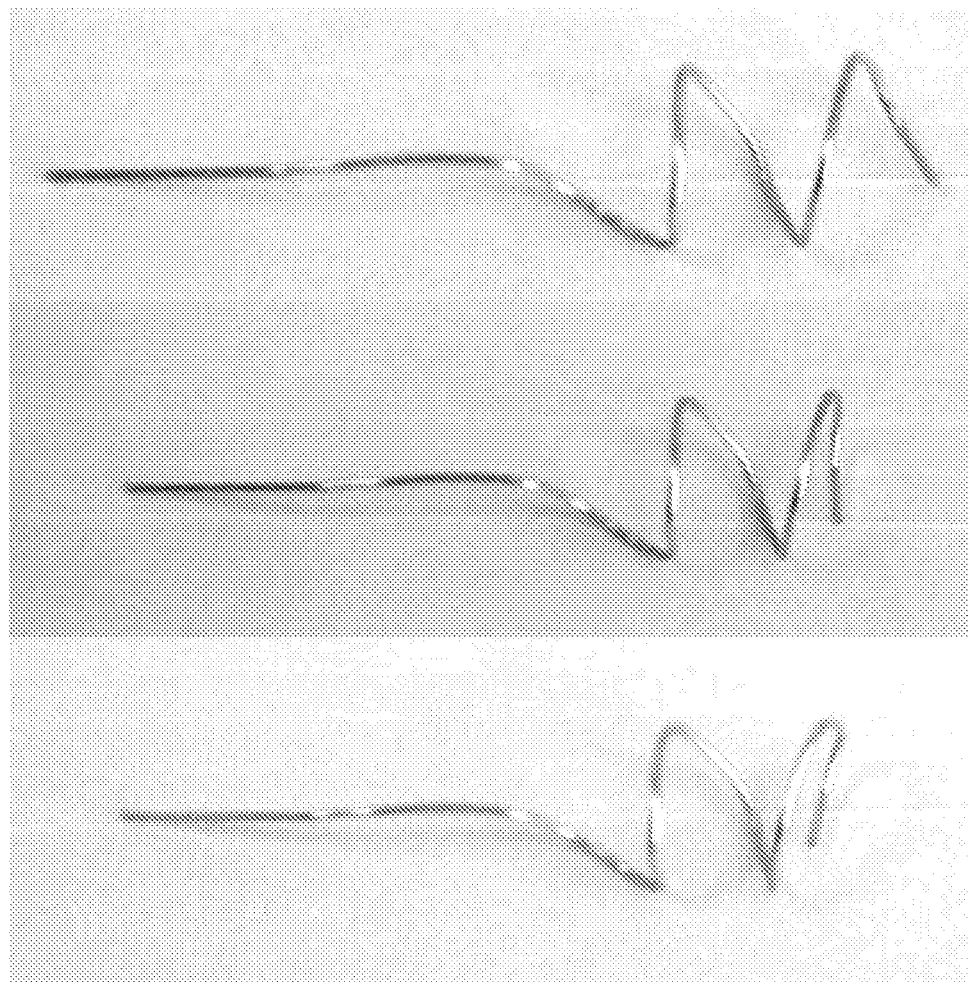
FIG. 9 shows models of three different embodiments of the geometry of the sharp distal tip of the ARD.

FIG. 9 shows models of three different possible embodiments of the ARD with different geometries of the distal tip. In the upper photograph, the tip of the ARD faces distally, that is, the tip has a forward pitch. In the middle photograph, the tip of the ARD lies in a plane perpendicular to the axis of the proximal portion, that is, the tip has a neutral pitch. In the bottom photograph the tip faces proximally, that is, the tip has a backward pitch. In this last embodiment, the distal-most point of the ARD is not the sharp tip. An ARD with a tip having a backward pitch could be particularly useful in repositioning the arytenoid by pulling. The backward pitch would make the device unlikely to accidentally disengaging. Likewise an ARD with a tip having a forward pitch could be particularly useful in repositioning the arytenoid by pushing. An ARD with a tip having a neutral pitch could be well-suited to either pushing or pulling the arytenoid.

Figure 10:
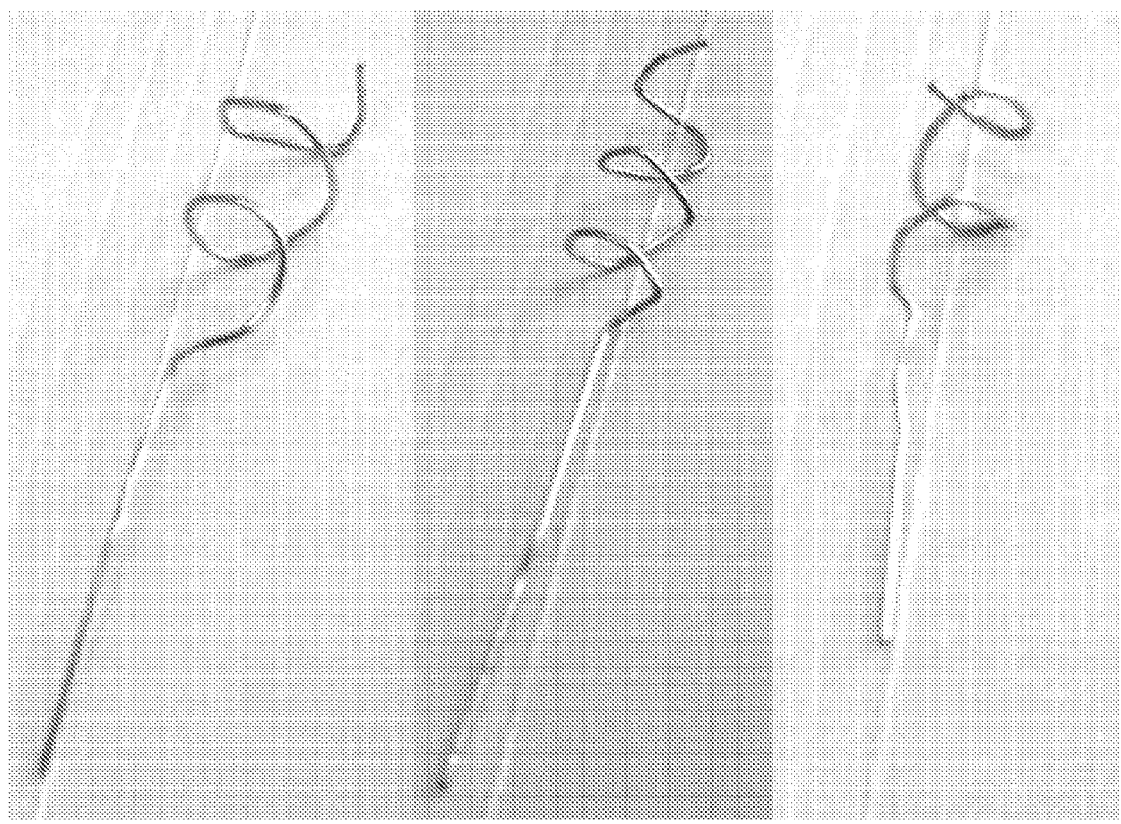
FIG. 10 shows models of three different embodiments of the geometry of the coil of the distal portion of the ARD.

FIG. 10 shows models of three different possible embodiments of the ARD with three different geometries of the coiled distal portion. The photograph on the left shows a left-handed coil. Proceeding along the coil from the proximal to the distal end, the wire proceeds counter-clockwise around the axis of the proximal portion. The photograph on the right shows a right-handed coil. Proceeding along the coil from the proximal to the distal end, the wire proceeds clockwise around the axis. The photograph in the middle shows a coil with a right-handed portion near the tip and a left-handed portion elsewhere. Proceeding along the coil from the proximal to the distal end, the wire at first proceeds counter-clockwise around the axis; but before reaching the tip, the coil reaches an inflection point and then proceeds clockwise to the tip.

I claim:

1. A method for repositioning a human subject's arytenoid cartilage using a kit, the kit comprising:
   a device for repositioning a human subject's arytenoid cartilage, comprising:
      a biocompatible wire comprising:
         an uncoiled, pliable proximal portion extending along an axis and having one or more recesses or protrusions positioned therealong; and
         a coiled distal portion terminating in a tip that is sufficiently sharp to penetrate human cartilage;
      wherein the wire is sized and shaped such that it permits repositioning of the arytenoid of the human subject by up to 10 millimeters while the tip engages the subject's arytenoid cartilage and while the proximal end is exterior to the subject's paraglottic space; and
      wherein the wire is sized and shaped such that it permits the tip to engage the subject's arytenoid cartilage while the proximal end is secured to the subject's thyroid cartilage;
   a threaded coupler capable of engaging the thyroid cartilage; and
   a fastener sized and shaped such that it may be attached to a thyroid cartilage of the human subject, the fastener defining a through hole for receiving the threaded coupler, the hole sized and shaped to allow the threaded coupler and the wire to simultaneously pass through the hole while the wire passes through the thyroid cartilage substantially non-perpendicular to the thyroid cartilage, the recesses or protrusions being sized and shaped to engage the fastener and secure the wire to the fastener when (a) the coupler and wire simultaneously pass through the hole, (b) the threaded coupler secures the fastener to the thyroid cartilage by engaging the thyroid cartilage, and (c) the threaded coupler partially obscures the hole;
   wherein the method comprises:
   making an incision in the subject's neck so as to allow access to the subject's cricothyroid membrane;
   advancing the device through the incision;
   further advancing the device through the subject's cricothyroid membrane into the paraglottic space;
   engaging a tissue of the subject with the distal end of the device, wherein the tissue comprises at least one of the subject's arytenoid muscular process, a thyroarytenoid muscle insertion, or a cricoarytenoid muscle insertion; and
   securing the proximal end of the device by passing the coupler and the wire simultaneously through the hole defined by the fastener, and affixing the coupler to a tissue of the patient, thereby affixing the fastener to at least one of the recesses or protrusions of the proximal end of the device.

2. The method of claim 1, wherein the tip of the device faces distally.

3. The method of claim 1, wherein the tip of the device faces proximally.

4. The method of claim 1, wherein the coiled distal portion of the device comprises a left-handed coil.

5. The method of claim 1, wherein the coiled distal portion of the device comprises a right-handed coil.

6. The method of claim 1, wherein the coiled distal portion of the device comprises both a left-handed coil and a right-handed coil.

7. The method of claim 1, wherein:
   the kit further comprises a hollow trocar having a proximal end, and a distal end, and defining an interior lumen, the trocar being so sized and shaped that the distal end of the device may be passed through the proximal end of the trocar, into the lumen, and out the distal end of the trocar; and
   the method further comprises the step of piercing the cricothyroid membrane with the trocar.

8. The method of claim 7, wherein further advancing comprises advancing the device through the trocar.

9. The method of claim 1, wherein the device, the coupler, and the fastener are the only objects permanently implanted in the subject.

10. The method of claim 1, wherein affixing comprises positioning the fastener anterior to the cricothyroid membrane.

11. The method of claim 1, wherein affixing comprises positioning the fastener snugly against an anterior aspect of the cricothyroid membrane.

12. The method of claim 1, wherein the tissue of the patient is a cartilage.

13. The method of claim 12, wherein the cartilage is the thyroid cartilage.

14. The method of claim 12 wherein securing comprises clamping the proximal end of the device between the cartilage and the at least one fastener such that the recesses or protrusions engage the fastener.

15. The method of claim 1 wherein the biocompatible wire is monolithic.

* * * * *